United States Patent [19]

Froehlich

[11] Patent Number: 4,526,174
[45] Date of Patent: Jul. 2, 1985

[54] STAPLE AND CARTRIDGE FOR USE IN A TISSUE STAPLING DEVICE AND A TISSUE CLOSING METHOD

[75] Inventor: Harold E. Froehlich, St. Anthony, Minn.

[73] Assignee: Minnesota Mining and Manufacturing Company, Saint Paul, Minn.

[21] Appl. No.: 550,053

[22] Filed: Nov. 7, 1983

Related U.S. Application Data

[63] Continuation of Ser. No. 248,575, Mar. 27, 1981, abandoned.

[51] Int. Cl.³ .............................................. A61B 17/10
[52] U.S. Cl. .................. 128/335; 128/334 R; 227/19; 227/120; 227/DIG. 1; 411/457; 206/438
[58] Field of Search .................. 128/334 R, 337, 335; 227/DIG. 1, 19, 120; 411/457; 206/438

[56] References Cited

U.S. PATENT DOCUMENTS 2,910,067  10/1959  White ............................. 128/334 R
4,014,492  3/1977  Rothfuss ..................... 227/DIG. 1 X
4,127,227  11/1978  Green ............................. 227/19 X

FOREIGN PATENT DOCUMENTS 67661  1/1915  Switzerland ..................... 128/337
1339394  12/1973  United Kingdom ............ 128/334 R Primary Examiner—Michael H. Thaler
Attorney, Agent, or Firm—Donald M. Sell; James A. Smith; William L. Huebsch

[57] ABSTRACT

A cartridge and method used for joining living tissue such as fascia. A staple in the cartridge having pointed arcuate end portions flanking a central portion is bent to provide a generally oval shape for the central portion and adjacent parts of the closed staple, and to bring the terminal parts of the staple into side-by-side crossed relationship with the points on each of the end portions positioned adjacent the central portion of the staple so that each of the end portions of the staple can extend through the tissue on one side of the closed opening and project into the tissue on the other side of the closed opening.

6 Claims, 12 Drawing Figures

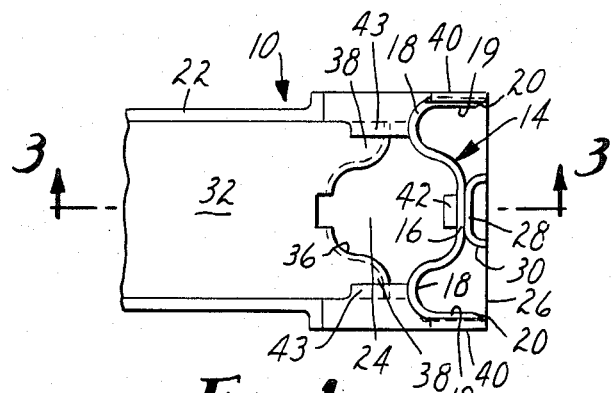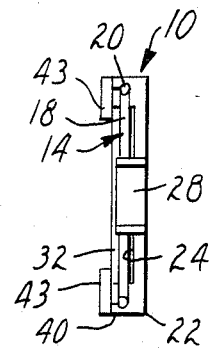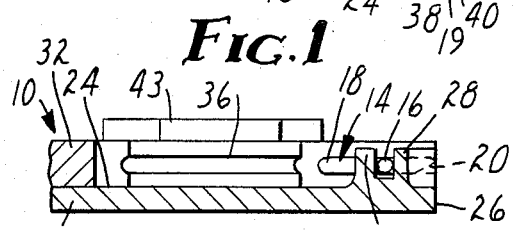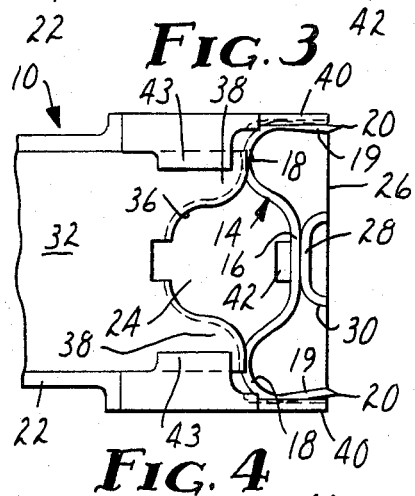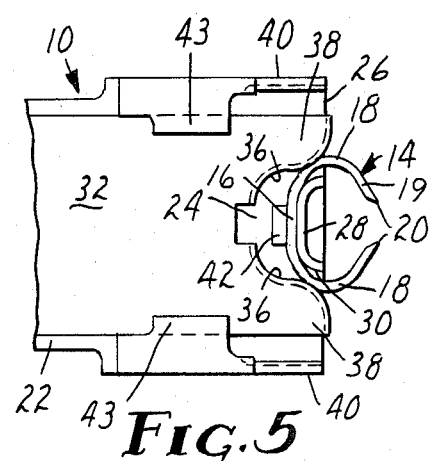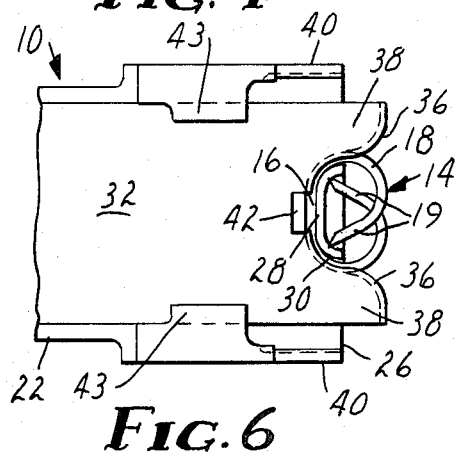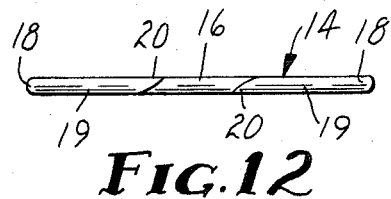

STAPLE AND CARTRIDGE FOR USE IN A TISSUE STAPLING DEVICE AND A TISSUE CLOSING METHOD

This is a continuation of application Ser. No. 248,575 filed Mar. 27, 1981, now abandoned.

TECHNICAL FIELD

This invention relates to staples, cartridges containing the staples adapted to be incorporated in staple-forming devices, and methods for fastening together separated living tissue, and particularly fascia, such as during a surgical operation.

BACKGROUND ART

Staples and cartridges containing the staples adapted to be incorporated in staple-forming devices intended for use to join separated fascia such as during an operation are known in the prior art. One such staple described in U.S. Pat. No. 4,014,492 has a straight central portion and pointed L-shaped portions at the ends of the central portion. A staple-forming device closes the staple by bending the junctures of the L-shaped portions and its central portion around the edges of an anvil so that the pointed ends of the L-shaped portions can engage and gather fascia. The closed staple assumes a rectangular shape with the points on the L-shaped portions generally aligned and closely adjacent. Such use of staples can provide much gather (the word "gather" as used herein means the ability of the staple and the device that closes the staple to draw together portions of fascia), which is very desirable so that the edges of the fascia attached will be pressed together to facilitate healing. The rectangular shape of the staple, however, allows the L-shaped legs to be too easily bent apart by tension in the gathered fascia so that the holding power of the staple is not as good as may be desired.

U.S. Pat. No. 4,127,227 describes a staple and a cartridge containing a plurality of the staples for use in a staple-forming device intended to correct the problem described above. Before it is closed, the staple described in that patent has a straight central portion with curved portions attached at each of its ends, which curved portions have points at their outermost ends adapted to engage fascia. By use of the cartridge in the staple-forming device, the curved end portions are each bent closed to form a closed staple with end loops each engaged only with one portion of the fascia to be joined. The closed loops are generally aligned with the central portion so that tension in the fascia does not act through a large lever arm in the closed loops to tend to open them. While such a closed staple structure minimizes problems with tension in the fascia opening the staple, the staple and its forming process provide very little gather so that fascia fastened by such staples may not be brought together to the degree desired by use of the staple and device.

DISCLOSURE OF INVENTION

The present invention provides a staple, a cartridge containing the staple adapted to be incorporated in a staple-forming device, and a method for joining living tissue, and particularly fascia, that will provide both a high degree of gather to ensure approximation of the tissue being joined to promote healing, and a closed staple shape that will strongly resist opening of the staple by tension in the tissue.

According to the present invention there is provided a cartridge adapted to be incorporated in a staple-forming device for use in joining separated or closing an opening in living tissue such as fascia. The cartridge includes at least one open staple comprising a length of wire having a central portion and having pointed arcuate end portions at opposite ends of the central portion, which staple is disposed with the points on the end portions and the central portion of the staple in general alignment. The cartridge also includes a frame comprising an anvil adapted to engage the central portion of the staple; and a ram movably mounted on the frame and having spaced projections and an end surface therebetween adapted to engage the end portions and bend the staple around the junctures between its end portions and its central portion to form the central portion and adjacent parts of the end portions generally into the shape of a single ellipse with the end portions in side-by-side crossed relationship at the side of the ellipse opposite the central portion and with the points on each of the end portions positioned adjacent the juncture between the central portion and the other of the end portions so that each of the end portions of the closed staple will extend through the fascia on one side of the closed opening and project into the fascia on the other side of the closed opening.

BRIEF DESCRIPTION OF DRAWING

The present invention will be further described with reference to the accompanying drawing wherein like numerals refer to like parts in the several views, and wherein:

FIG. 1 is a plan view of a cartridge according to the present invention;

FIG. 2 is an end view of the cartridge shown in FIG. 1;

FIG. 3 is a sectional view taken approximately along the line 3—3 of FIG. 1;

FIGS. 4 through 6 are enlarged views sequentially showing closing of a staple included in the cartridge of FIG. 1;

FIG. 12 is an enlarged front view of the staple as shown in FIGS. 5 and 8.

DETAILED DESCRIPTION

Figure 7:
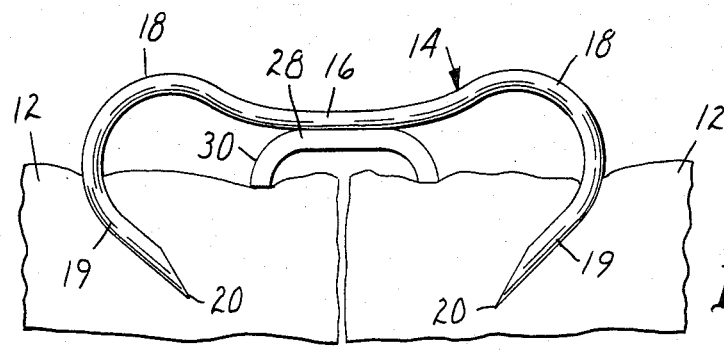
FIGS. 7 through 11 are enlarged views sequentially showing the engagement of the staple in the cartridge shown in FIG. 1 with portions of living tissue as the staple is closed in accordance with a method according to the present invention.

Referring now to the drawing, there is shown a cartridge 10 according to the present invention which is adapted to be removably incorporated in a staple-forming device (not shown) intended for use in joining separated living tissue such as fascia 12.

The cartridge 10 comprises at least one open staple 14 comprising a length of wire having a straight or slightly curved central portion 16, and arcuate end portions 18 including straight or slightly curved terminal end parts 19 having points 20 on their ends opposite the central portion 16, with the points 20 on the end portions 18 and the central portion being generally aligned (e.g., with 0.06 inch alignment).

Figure 11:
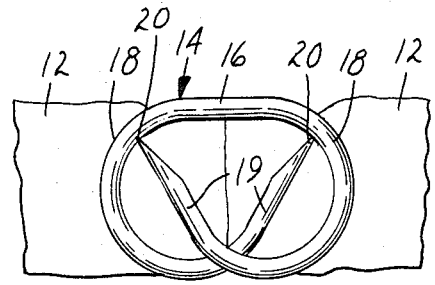

The cartridge 10 includes a frame 22 having a planar support surface 24, and means for supporting the staple 14 with its side surfaces parallel to the support surface 24 and the points 20 of the staple 14 adjacent an end 26 of the frame 22, and an anvil 28 projecting at approximately a right angle to the support surface 24 centrally of the staple 14, which anvil 28 has an arcuate surface 30 adapted to be engaged by the central portion 16 and adjacent parts of the end portions 18 of the staple 14. Also included is a ram 32, and means mounting the ram 32 for movement along the planar support surface 24 from a spaced position (FIGS. 1, 2 and 3) affording placing the open staple 14 against the anvil 28, toward the anvil 28 so that a transversely grooved end surface 36 extending between spaced projections 38 of the ram 32 will engage and bend the staple 14 around the juncture between its central and end portions (FIGS. 4, 5 and 6). Such bending will form a generally oval or elliptical shape for the central portion 16 and adjacent parts of the end portions 18 of the staple 14 (FIG. 6) and will bring the terminal end parts 19 of the end portions of the staple 14 into side-by-side crossed relationship at the side of the ellipse opposite the central portion 16 with the points 20 of each of the end portions 18 positioned adjacent the juncture between the central portion 16 and the other of the end portions 18. By "adjacent the juncture between the central portion 16 and the other of the end portions 18" we mean that the terminal end parts 19 can cross, terminate at (FIG. 11), or terminate within (FIG. 6) the outer portions of the staple either at or outboard of the juncture; and, particularly with curved terminal end parts 19, could lay approximately along the other of the end portion 18.

The cartridge 10 could be adapted for use in any one of several staple-forming devices (not shown) which afford releasable engagement of the frame 22 of the cartridge 10 with the frame of the device, and which have mechanisms that the ram 32 can be adapted to engage which can be activated either manually or by an electrical or air power supply to provide reciprocal rectilinear movement of the ram 32. One such device is described in U.S. Pat. No. 3,949,924.

Also, it is expected that the cartridge could be modified to utilize one of many known types of magazines to feed staples seriatim to the anvil via the operation of the device as each staple at the anvil is engaged with tissue. As illustrated, however, the cartridge 10 contains only the single staple 14 which is initially held in place by means including opposed longitudinally extending grooves in portions of upstanding edge walls 40 on the frame 22, in which grooves the outer surfaces of the terminal end parts 19 of the staple 14 are frictionally held, and a projecting block 42 that engages the central portion 16 of the staple 14 on its side opposite the anvil 28 to prevent it from bowing away from the anvil 28 as the staple 14 is closed.

The means mounting the ram 32 on the frame 22 comprise the support surface 24 along which the ram 32 slides, portions of the upstanding edge walls 40 which guide the edges of the ram 32, and tabs 43 which extend over the ram 32 in spaced relationship to the surface 24 to retain the ram 32 against the surface 24. The transverse groove in the end surface 36 of the ram 32 engages and maintains the staple 14 in alignment as it is formed around the anvil 28. The end surface 36, as viewed from the support surface 24, is generally bell-shaped with a central cavity having a generally oval or elliptical shape corresponding to the elliptical shape to be formed in the central portion 16 and adjacent parts of the staple 14, which oval shape of the end surface 30 is interrupted only by a central notch adapted to receive the block 42 as the ram 32 moves to form the staple 14.

FIGS. 7 through 11 illustrate the engagement of the staple 14 with tissue or fascia 12 and the gather produced by such engagement.

Figure 8:
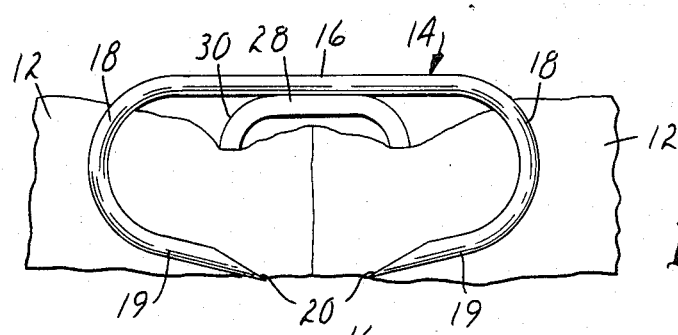
Figure 9:
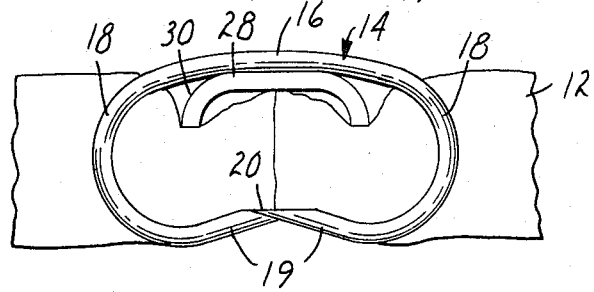
Figure 10:
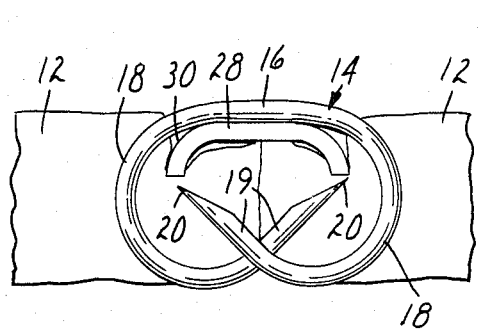

After engagement of the points 20 of the staple 14 with the fascia 12, the staple 14 is closed by bending it through almost 180 degrees around the junctures between its central portion 16 and its end portions 18. As the staple enters the fascia 12 (FIG. 7), it begins to draw the portions of fascia 12 together and enters the fascia 12 to a predetermined depth controlled by the diameter of the arc in its end portions 18 (FIG. 8). Such depth control can be important to prevent piercing of body portions beneath the fascia 12. Subsequently the terminal end parts 19 of the staple 14 will move past each other (FIG. 9). Such passing of the terminal end parts 19 is facilitated by shearing the staple 14 from different sides to form the points 20, which, as can be seen in FIG. 12, moves the points 20 to opposite sides of the staple 14 so that the points 20 will not meet and the tapered terminal end parts 19 can slide by each other. Each end portion 18 will then enter the portion of fascia 12 through which the other end portion 18 extends (FIG. 10) and move to a position with its point 20 adjacent the juncture between the central portion 16 and the other end portion 18 (FIG. 11) whereupon the anvil 28 is withdrawn. The resultant closed shape of the staple (FIG. 11) will strongly resist opening because tension in the fascia 12 acts through a very short lever arm against the generally oval central portion 16 and adjacent parts of the end portions 18.

Such closure of the staple will gather the tissue 12 by an amount related to the difference in width between the points 20 of the open staple 14 as they enter the tissue 12, and the inner width of the closed staple in which the tissue 12 engaged by the points 20 is contained. Such gather can be expressed as a percentage by dividing that difference in width by the width between the points 20 of the open staple 14. Using such a computation it has been found that the staple 14 closed in the manner illustrated and described above can provide gather in the range of 60 to 70 percent.

I claim:

1. A cartridge adapted to be incorporated in a staple-forming device for use in closing an opening in living tissue including fascia, said cartridge comprising at least one open staple comprising a length of wire having a central portion, and arcuate end portions at opposite ends of the central portion having points at their ends opposite said central portion, with the points on said end portions and said central portion being generally aligned; a frame comprising an anvil adapted to engage said central portion; and a ram movably mounted on said frame and having spaced projections and an arcuate recessed end surface therebetween adapted to engage said end portions and bend said staple around the juncture between said end portions and said central portion to form the central portion and adjacent parts of said end portions generally into the shape of a single ellipse with the difference between the inner width dimension of the ellipse and the dimension between the points of the open staple being up to about 70 percent of the dimension between the points of the open staple to provide a substantial amount of gather for the living tissue defining the opening, with said end portions in side-by-side crossed relationship at the side of the ellipse opposite said central portion, and with the points on each of the end portions positioned adjacent the juncture between the central portion and the other of the end portions so that each of said end portions of the staple when closed can extend through the tissue on one side of the closed opening and project into the tissue on the other side of the closed opening.

2. A cartridge according to claim 1 wherein the difference between the inner width dimension of the ellipse and the dimension between the points of the open staple is in the range of about 60 to 70 percent of the dimension between the points of the open staple.

3. A method for closing an opening in living tissue such as fascia comprising the steps of:

providing a staple comprising a length of wire having a central portion joining arcuate end portions, which end portions have points at their distal ends with the points on said end portions and said central portion being generally aligned;

engaging the pointed ends with tissue to be joined; and bending the staple around its juncture between its end portions and its central portion to cause the pointed end portions to pierce through the engaged tissue, and to form the central portion and adjacent parts of the end portions generally into the shape of a single ellipse with the difference between the inner width dimension of the ellipse and the dimension between the points of the open staple being up to about 70 percent of the dimension between the points of the open staple to provide a substantial amount of gather for the living tissue defining the opening, with the end portions in side-by-side crossed relationship at the side of the ellipse opposite the central portion and bridging between the pierced portions of the tissue, and with each of the terminal end parts of the end portions within the portion of the tissue pierced by the other part and at a position with its point adjacent the juncture between the central portion and the other of the end portions.

4. A method according to claim 3 wherein said bending step comprises the steps of supporting the central portion of the staple against an anvil, and pushing on said end portions to bend them around said anvil.

5. A method according to claim 3 wherein the difference between the inner width dimension of the ellipse and the dimension between the points of the open staple is in the range of about 60 to 70 percent of the dimension between the points of the open staple.

6. A staple for use in closing an opening in living tissue, including fascia, said staple, when open, comprising a length of wire having a central portion, and arcuate end portions at opposite ends of the central portion having points at their ends opposite said central portion, with the points on said end portions and said central portion being generally aligned; which staple, when closed, is bent around the juncture between said end portions and said central portion to form the central portion and adjacent parts of said end portions generally into the shape of a single ellipse with the difference between the inner width dimension of the ellipse and the dimension between the points of the open staple being in the range of about 60 to 70 percent of the dimension between the points of the open staple to provide a substantial amount of gather for the living tissue defining the opening, with said end portions in side-by-side crossed relationship at the side of the ellipse opposite said central portion, and with the points on each of the end portions positioned adjacent the juncture between the central portion and the other of the end portions so that each of said end portions of the staple can extend through the tissue on one side of the closed opening and project into the tissue on the other side of the closed opening.

* * * * *